(12) United States Patent
Komada et al.

(10) Patent No.: US 11,675,141 B2
(45) Date of Patent: Jun. 13, 2023

(54) OPTICAL CONNECTOR FERRULE, OPTICAL CONNECTOR, AND COMPOSITE FIBER CONNECTING ASSEMBLY

(71) Applicants: KYOCERA Corporation, Kyoto (JP); TOHOKU UNIVERSITY, Sendai (JP)

(72) Inventors: Daisuke Komada, Omihachiman (JP); Hiroki Tachibana, Kitami (JP); Ko Matsui, Sendai (JP); Yuanyuan Guo, Sendai (JP)

(73) Assignees: KYOCERA Corporation, Kyoto (JP); TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 17/270,888

(22) PCT Filed: Aug. 30, 2019

(86) PCT No.: PCT/JP2019/034287
§ 371 (c)(1),
(2) Date: Feb. 24, 2021

(87) PCT Pub. No.: WO2020/045669
PCT Pub. Date: Mar. 5, 2020

(65) Prior Publication Data
US 2021/0181434 A1 Jun. 17, 2021

(30) Foreign Application Priority Data
Aug. 31, 2018 (JP) .............................. JP2018-163950

(51) Int. Cl.
*G02B 6/38* (2006.01)

(52) U.S. Cl.
CPC ......... *G02B 6/3882* (2013.01); *G02B 6/3817* (2013.01); *G02B 6/3885* (2013.01)

(58) Field of Classification Search
CPC ... G02B 6/3817; G02B 6/3882; G02B 6/3885
See application file for complete search history.

(56) References Cited

U.S. PATENT DOCUMENTS

| 7,572,063 B2 * | 8/2009 | Mynott | G02B 6/3817 385/79 |
| 9,500,812 B2 * | 11/2016 | Tanaka | G02B 6/3817 |

(Continued)

FOREIGN PATENT DOCUMENTS

| JP | 06-222236 A | 8/1994 | |
| JP | 2014011050 A * | 1/2014 | ........... G02B 6/3817 |

OTHER PUBLICATIONS

Andres Canales, et al. "Multifunctional fibers for simultaneous optical, electrical and chemical interrogation of neural circuits in vivo", Nature Biotechnology, 33, 277-284 (2015).

*Primary Examiner* — Daniel Petkovsek
(74) *Attorney, Agent, or Firm* — Volpe Koenig

(57) ABSTRACT

An optical connector ferrule, an optical connector, and a composite fiber connecting assembly are provided. The optical connector ferrule includes a stationary ferrule having a first through-hole, a composite fiber, and a connecting ferrule having a second through-hole. The composite fiber includes a first optical fiber and a signal wire, and is placed in the first through-hole in the stationary ferrule. The connecting ferrule includes a conductive path. The stationary ferrule has a second end face abutting a third end face of the connecting ferrule. The first optical fiber has an end connected to an end of the second through-hole. The signal wire and the conductive path are connected to each other.

8 Claims, 11 Drawing Sheets

(56) References Cited

U.S. PATENT DOCUMENTS

| | | | | |
|---|---|---|---|---|
| 10,016,136 B2* | 7/2018 | Labrie | .................. | A61B 5/0084 |
| 2004/0218873 A1* | 11/2004 | Nagashima | .......... | G02B 6/4284 |
| | | | | 385/75 |
| 2011/0033155 A1* | 2/2011 | Daikuhara | ........... | G02B 6/3817 |
| | | | | 427/125 |
| 2011/0224554 A1 | 9/2011 | Vukeljic et al. | | |
| 2011/0243508 A1* | 10/2011 | Koreeda | .............. | G02B 6/3817 |
| | | | | 385/78 |

\* cited by examiner

… (1 / 9)

OPTICAL CONNECTOR FERRULE, OPTICAL CONNECTOR, AND COMPOSITE FIBER CONNECTING ASSEMBLY

FIELD

The present disclosure relates to an optical connector ferrule, an optical connector, and a composite fiber connecting assembly.

BACKGROUND

To record information about the brain neural activity of small animals such as rodents (e.g., mice and rats) and marmosets as electrical signals for a predetermined period, one known method is to insert and fix wire electrodes in the living brains of such animals. To obtain more information, the living brains may be stimulated by light illumination or by drug administration. The reactions may then be recorded as electrical signals. The states of the living brain surfaces may also be recorded as images formed using light reflected from the surfaces. In addition to wire electrodes, multifunctional fibers have been developed, each combining multiple paths including an optical path for light illumination or light reception and paths for drugs or other uses (refer to, for example, Non-Patent Literature 1).

CITATION LIST

Non-Patent Literature

Non-Patent Literature 1: Andres Canales, et al. "Multifunctional fibers for simultaneous optical, electrical and chemical interrogation of neural circuits in vivo", Nature Biotechnology, 33, 277-284 (2015)

BRIEF SUMMARY

An optical connector ferrule according to one aspect of the present disclosure includes a first ferrule, a composite fiber, and a second ferrule. The first ferrule is tubular and has a first end face, a second end face opposite to the first end face, and a first through-hole extending from the first end face to the second end face. The composite fiber includes a first optical fiber and a through-portion along the first optical fiber. The composite fiber has a first end portion extending to the second end face and placed in the first through-hole. The second ferrule includes a ferrule body being tubular and a linear portion. The ferrule body has a third end face, a fourth end face opposite to the third end face, and a second through-hole extending from the third end face to the fourth end face. The linear portion extends from the third end face along the second through-hole. The second end face and the third end face abut each other. The through-portion and the linear portion are connected to each other.

An optical connector according to another aspect of the present disclosure includes the optical connector ferrule according to the above aspect, and a sleeve enclosing an area in which the second end face and the third end face abut each other.

A composite fiber connecting assembly according to still another aspect of the present disclosure includes the optical connector according to the above aspect, and a second optical fiber in the second through-hole to optically couple a first end of the first optical fiber and a third end of the second optical fiber at the third end face of the ferrule body.

A connecting ferrule according to still another aspect of the present disclosure includes a ferrule body being tubular and a linear portion. The ferrule body has a third end face, a fourth end face opposite to the third end face, and a second through-hole extending from the third end face to the fourth end face. The linear portion extends along the second through-hole.

DETAILED DESCRIPTION

Figure 1:
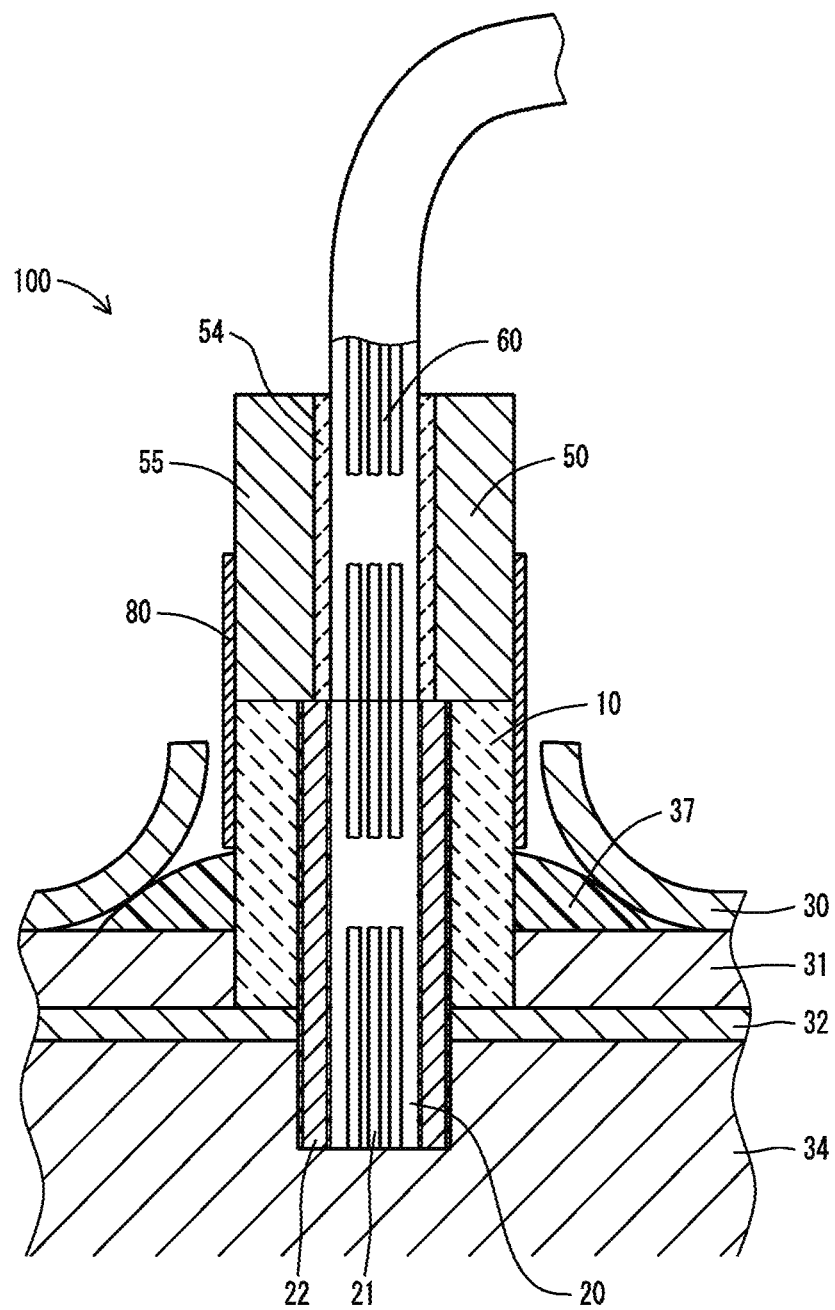
FIG. 1 is a cross-sectional view of a composite fiber connecting assembly according to a first embodiment of the present disclosure.

A composite fiber connecting assembly according to one or more embodiments of the present disclosure will now be described with reference to the drawings. FIG. 1 is a cross-sectional view of a composite fiber connecting assembly according to a first embodiment of the present disclosure. A composite fiber connecting assembly 100 in the present embodiment may be used to obtain information about the brain neural activity of small animals for experimentation such as rodents and marmosets or to observe their brain cells responding to electrical signals or liquid drugs. In FIG. 1, a composite fiber including an optical fiber and one or more signal wires is installed inside the brain. The composite fiber connecting assembly 100 may transfer and receive optical signals, electrical signals, or liquid drugs to and from another component fixed to the brain. In some embodiments, the composite fiber connecting assembly 100 may be used without being fixed to the brain or other parts. When the composite fiber connecting assembly 100 is used without being fixed, a stationary ferrule (described later) may be gripped using a manipulator. The composite fiber connecting assembly 100 may be placed at deeper or less deep positions with a manipulator for every measurement.

In actual use of the composite fiber, for example, an optical fiber that serves as an optical path is connected to a light emitter-receiver, an electrode wire is connected to an electrical signal transmitter-receiver, and a path is connected to a liquid drug tank or to a liquid feeder with a tube. A known composite fiber has a diameter of about 200 to 500 μm and is thus to be connected to such an external device manually with a microscope. This is time-consuming and involves work by a skilled operator. One or more aspects of the present disclosure are directed to an optical connector ferrule, an optical connector, and a composite fiber connecting assembly that allow easy connection of a composite fiber to an external device in a short time.

The composite fiber connecting assembly 100 includes two sections, one section to be fixed to the brain of a small animal for experimentation and the other section to receive an external connection. The section to be fixed includes a stationary ferrule 10 and a composite fiber 20. The section to receive an external connection includes a connecting ferrule 50 and a second optical fiber 60. The structure of these two sections will now be described.

Figure 2A:
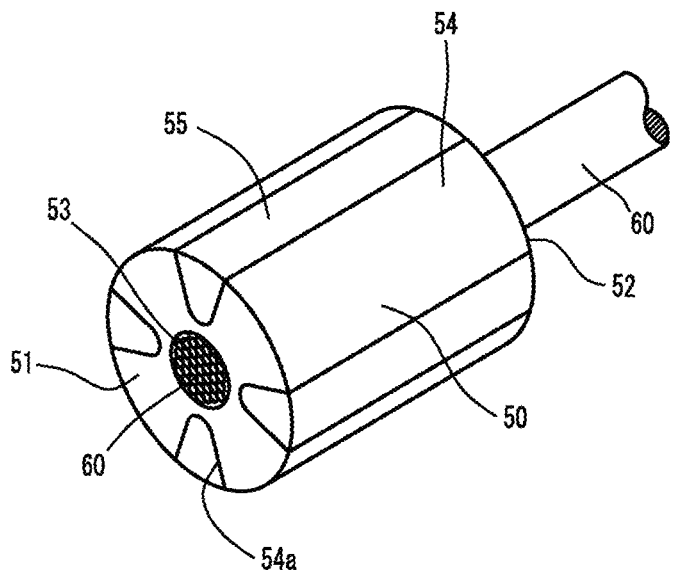
FIG. 2A is a perspective view of a connecting ferrule according to the first embodiment and an external optical fiber.
Figure 2B:
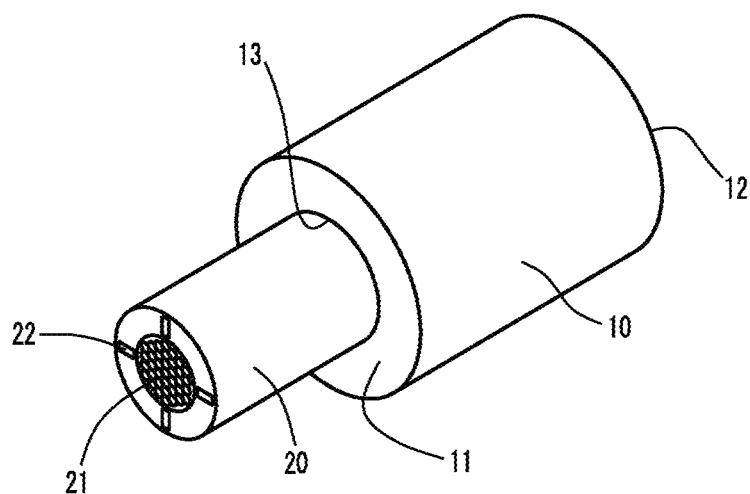
FIG. 2B is a perspective view of a stationary ferrule and a composite fiber in the first embodiment.
Figure 3A:
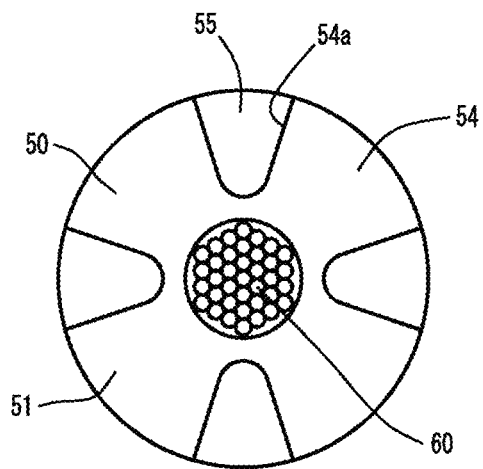
FIG. 3A is an end view of the connecting ferrule in the first embodiment.
Figure 3B:
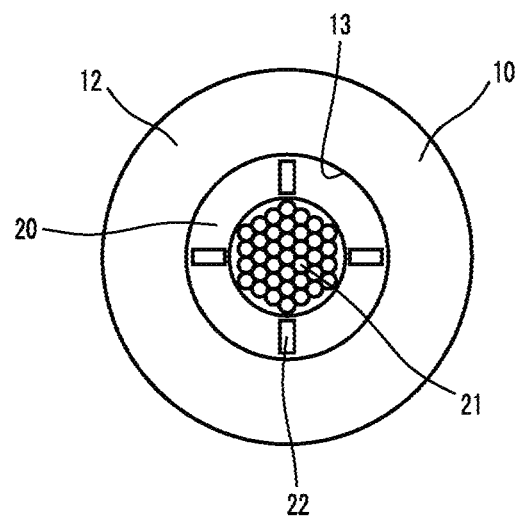
FIG. 3B is an end view of the stationary ferrule in the first embodiment.

FIG. 2A is a perspective view of the connecting ferrule according to the first embodiment and an external optical fiber. FIG. 2B is a perspective view of the stationary ferrule and the composite fiber in the first embodiment. FIG. 3A is an end view of the connecting ferrule in the first embodiment. FIG. 3B is an end view of the stationary ferrule in the first embodiment. The stationary ferrule 10 is a tubular first ferrule having a first end face 11, a second end face 12 opposite to the first end face 11, and a first through-hole 13 extending from the first end face 11 to the second end face 12. The stationary ferrule 10 in the present embodiment is cylindrical, but may be tubular in any shape. The first through-hole 13 in the present embodiment has an inner diameter sized in correspondence with the outer profile of the composite fiber 20 to be placed in the first through-hole 13. The composite fiber 20 includes a first optical fiber 21, and one or more signal wires 22 (through-portion) along the first optical fiber 21. The composite fiber 20 is placed in the first through-hole 13 to have a first end portion 24 at the second end face 12. The composite fiber 20 protrudes axially outward from the first end face 11 of the stationary ferrule 10. The stationary ferrule 10 is placed, for example, through a scalp 30 and a skull 31 of a head of a living small animal for experimentation. The stationary ferrule 10 is fixed to have the first end face 11 on a brain 34 and the second end face 12 to receive external connection. The stationary ferrule 10 is fixed in the head by an operator gripping the stationary ferrule 10 with a manipulator and attaching the stationary ferrule 10 to a site of the brain 34 to be measured. The stationary ferrule 10 is firmly fixed to the skull 31 with a bond 37 formed from dental cement. The stationary ferrule 10 may be fixed using multiple different bonds 37 in layers.

The composite fiber 20 is inserted in the first through-hole 13 in the stationary ferrule 10 attached to a predetermined measurement site of the head. As described above, the composite fiber 20 includes the first optical fiber 21 to emit or receive light to or from brain cells, and the signal wire(s) 22 around and along the first optical fiber 21. The first optical fiber 21 may be a single optical fiber, or may be a bundle of multiple optical fibers. In the bundle of multiple optical fibers, each fiber receives light reflected from the measurement site to obtain image data including pixels of light received by the respective fibers. Light from brain cells may be the luminescence or fluorescence emitted by the brain cells. The brain cells may emit fluorescence in response to external excitation light.

The signal wire 22 is a wire of conductive material buried in a resin portion encapsulating the first optical fiber 21. The conductive material may be, for example, carbon (carbon nanofiber) or a Bi—Sn alloy. The signal wire 22 can carry an externally input electrical signal to electrically stimulate brain cells or can carry and output an electrical signal generated from the brain cells. The composite fiber 20 may include one or more signal wires 22, one or all of which may be used depending on each experiment. The composite fiber 20 has a second end portion 25 placed in the brain 34, at which light and electrical signals are input and output.

The connecting ferrule 50 is a second ferrule including a tubular ferrule body 54 having a third end face 51, a fourth end face 52 opposite to the third end face 51, a second through-hole 53 extending from the third end face 51 to the fourth end face 52, and one or more conductive paths 55 extending along the second through-hole 53 and partially exposed at the third end face 51. In the present embodiment, the ferrule body 54 has the second through-hole 53 around which one or more grooves 54a extend axially, and the conductive path 55 defined in each groove 54a. The connecting ferrule 50 includes one or more conductive paths 55 corresponding to the number of signal wires 22 in the composite fiber 20.

The conductive path 55 is linear. The conductive path 55 may be, for example, a conductive paste containing a conductive material filling the groove 54a, a conductive wire such as a thin metal wire placed and fixed in the groove 54a, or a conductive wire buried in a conductive paste in the groove 54a. In the present embodiment, the conductive path 55 extends from the third end face 51 along the second through-hole 53. For electrical connection with the signal wire 22 in the composite fiber 20 as described below, the conductive path 55 is partially exposed at the third end face 51, while either being exposed or without being exposed at the fourth end face 52. For electrical connection with an external device, the conductive path 55 may be partially exposed at any position other than the third end face 51. The conductive path 55 may then be connected to an external device through the exposed portion. For example, the conductive path 55 including a conductive wire described above may be directly connected to an external device using, for example, a long conductive wire as a lead wire.

The second optical fiber 60 may have one end (third end) at the third end face 51 of the connecting ferrule 50 and may be optically coupled to the first optical fiber 21 in the composite fiber 20. The first optical fiber 21 may have the same fiber diameter (core diameter) as or a different fiber diameter from the second optical fiber 60. In the present embodiment, the first optical fiber 21 is a bundle of multiple optical fibers, and the second optical fiber 60 has the same structure as the first optical fiber 21 and is also a bundle of multiple optical fibers. In some embodiments, the second optical fiber 60 may be a single optical fiber. The second optical fiber 60 has the other end extending further from the connecting ferrule 50 and connected to an external device. The second optical fiber 60 as a bundle of multiple optical fibers may include more fibers than the first optical fiber 21. Each fiber of the second optical fiber 60 may have a smaller core diameter than each fiber of the first optical fiber 21. This structure allows the light emitting portion to have higher precision and to form an image with higher definition (resolution).

Figure 4:
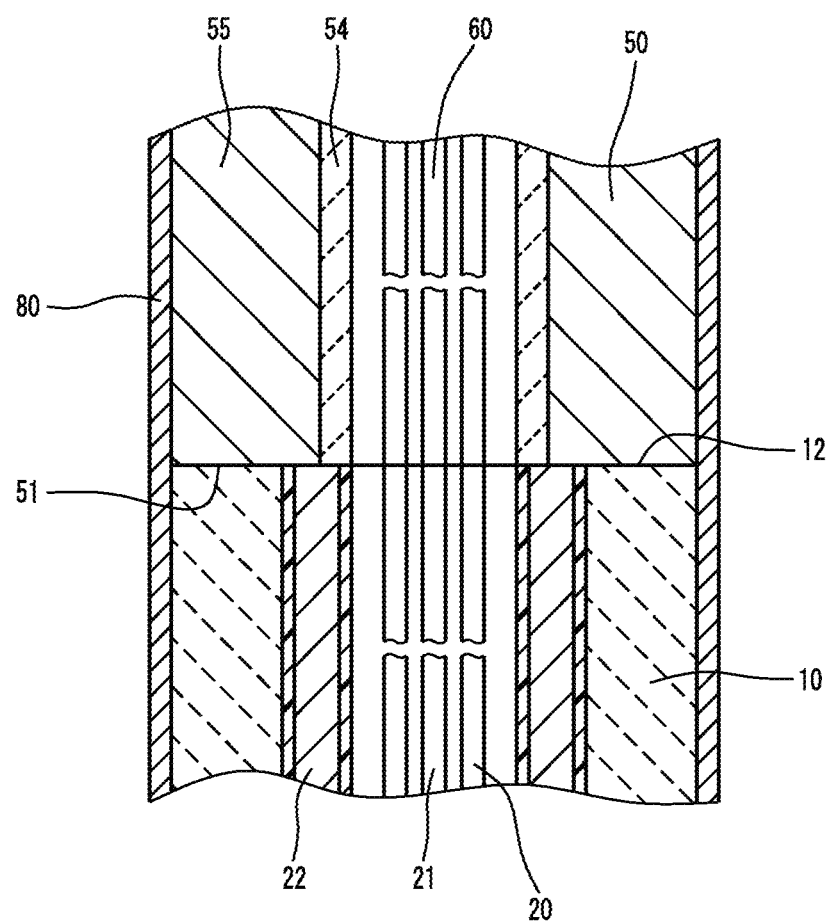
FIG. 4 is a partially enlarged cross-sectional view of the composite fiber connecting assembly in the first embodiment.

FIG. 4 is a partially enlarged cross-sectional view of the composite fiber connecting assembly in the first embodiment. The stationary ferrule 10 and the connecting ferrule 50 are placed to have the second end face 12 and the third end face 51 abutting each other. In the present embodiment, the second end face 12 and the third end face 51 abut each other and are in contact with each other. The first optical fiber 21 has an end (first end) at the second end face 12 connected to an end (second end) of the second through-hole 53 at the third end face 51. The second through-hole 53 receives the second optical fiber 60. The second optical fiber 60 has the end located in the end of the second through-hole 53 at the third end face 51. More specifically, the end of the first optical fiber 21 at the second end face 12 is optically coupled to the end of the second optical fiber 60 at the third end face 51. Each signal wire 22, as a through-portion extending through the composite fiber 20, is electrically connected to the conductive path 55.

The composite fiber 20 is installed beforehand in the first through-hole 13 in the stationary ferrule 10 and fixed to the skull 31, whereas the second optical fiber 60 is placed in the second through-hole 53 in the connecting ferrule 50. The connection work is simply to place the third end face 51 of the connecting ferrule 50 into contact with the second end face 12 of the fixed stationary ferrule 10. The connecting ferrule 50 is connectable to an external device. This structure allows easy connection of the composite fiber to an external device in a short time. For easier connection work, a sleeve 80 is used in the present embodiment. The sleeve 80 is a tubular member externally set on the stationary ferrule 10 and the connecting ferrule 50. The sleeve 80, the stationary ferrule 10, and the connecting ferrule 50 are coaxial. The sleeve 80 encloses the second end face 12 of the stationary ferrule 10. The sleeve 80 has a portion protruding outward from the second end face 12 to define a space between its inner peripheral surface and the second end face 12. The connecting ferrule 50 is fitted into the sleeve 80 to have their axes aligned with each other. When the connecting ferrule 50 is abutted against the stationary ferrule 10, the second end face 12 of the stationary ferrule 10 and the third end face 51 of the connecting ferrule 50 come in contact with each other. The sleeve 80 may be a split sleeve with a slit across its length.

The stationary ferrule 10 and the ferrule body 54 of the connecting ferrule 50 are formed from a ceramic material. Examples of the ceramic material include alumina ($Al_2O_3$), zirconia ($ZrO_2$), aluminum nitride (AlN), silicon carbide (SiC), silicon nitride ($Si_3N_4$), forsterite ($2MgO \cdot SiO_2$), sialon (SiAlON), barium titanate ($BaTiO_3$), lead zirconate titanate (PZT), ferrite, and mullite. Among these ceramic materials, zirconia has high biocompatibility. When zirconia is used as the ceramic material, an additive may be used. The additive may be, for example, a stabilizer such as yttria.

The stationary ferrule 10 and the ferrule body 54 may be prepared through the processes described below. First, a powder of a ceramic material such as zirconia is kneaded with a binder into a mixture. The binder may be selected as appropriate, and may be a thermoplastic polymer or a hydrophilic polymer. The mixture is pressure-molded using a mold having a cavity with a predetermined shape to be the stationary ferrule 10 and the ferrule body 54 to produce a molded body. The molded body is then fired at temperatures of about 1300 to 1400° C. Through the above processes, the stationary ferrule 10 and the ferrule body 54 are formed from a ceramic material such as zirconia.

The conductive path 55 of the connecting ferrule 50 is formed from a metal material, such as copper, silver, or gold. The metal material may be a metal wire or a metal paste (or a solid paste). For example, the conductive path 55 may be a copper wire. The copper wire as the conductive path 55 may be fixed to the ferrule body 54 with, for example, a resin adhesive. The conductive path 55 may be formed from, for example, a Bi—Sn alloy.

Figure 5A:
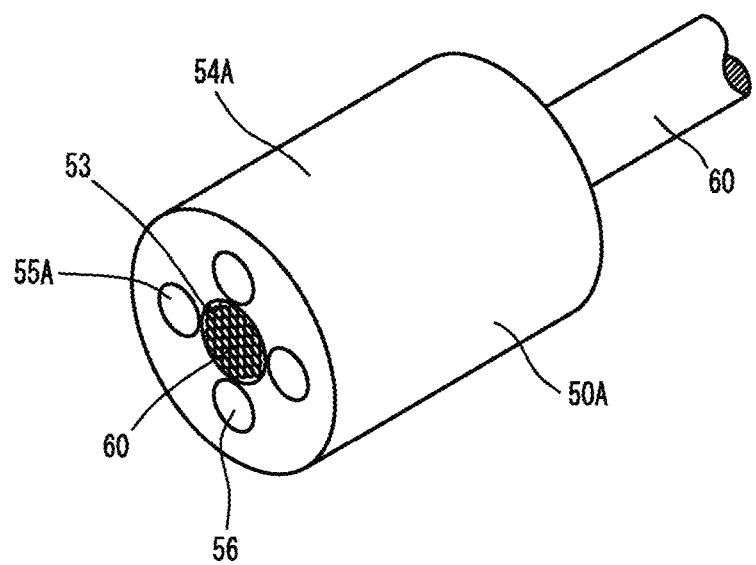
FIG. 5A is a perspective view of a connecting ferrule according to a second embodiment and an external optical fiber.
Figure 5B:
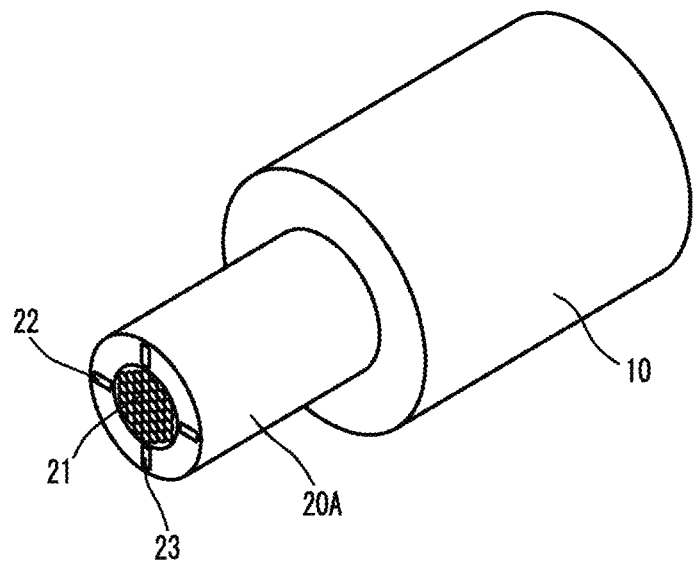
FIG. 5B is a perspective view of a stationary ferrule and a composite fiber in the second embodiment.
Figure 6A:
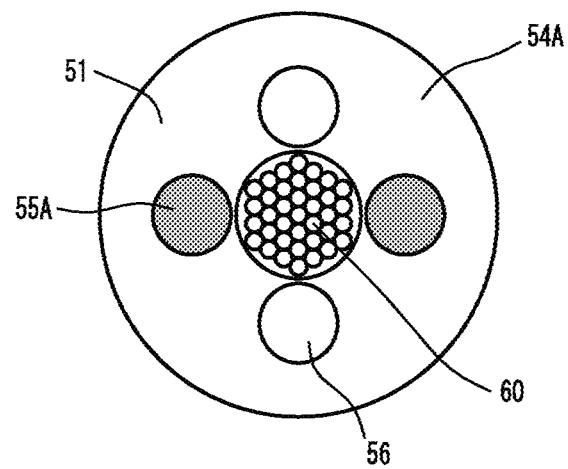
FIG. 6A is an end view of the connecting ferrule in the second embodiment.
Figure 6B:
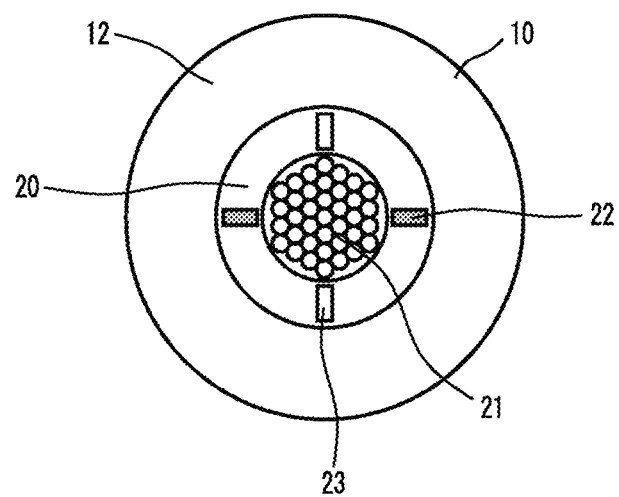
FIG. 6B is an end view of the stationary ferrule in the second embodiment.
Figure 7:
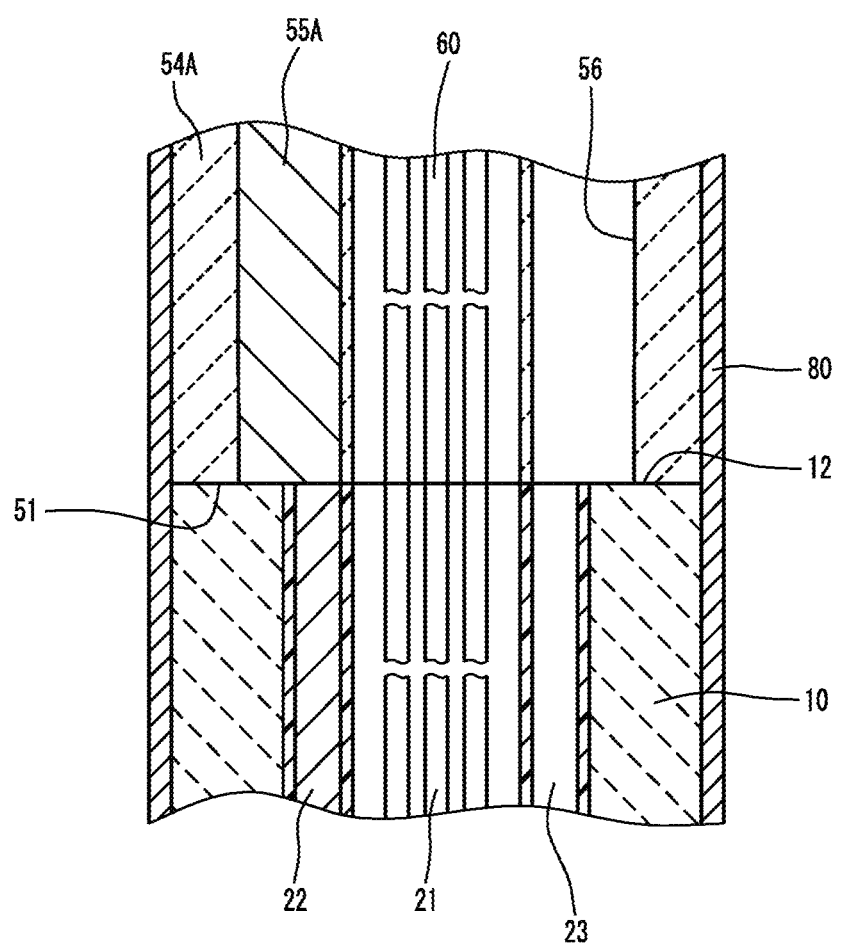
FIG. 7 is a partially enlarged cross-sectional view of a composite fiber connecting assembly according to the second embodiment.

A second embodiment will now be described. FIG. 5A is a perspective view of a connecting ferrule according to the second embodiment and an external optical fiber. FIG. 5B is a perspective view of a stationary ferrule and a composite fiber in the second embodiment. FIG. 6A is an end view of the connecting ferrule in the second embodiment. FIG. 6B is an end view of the stationary ferrule in the second embodiment. FIG. 7 is a partially enlarged cross-sectional view of a composite fiber connecting assembly according to the second embodiment. The second embodiment differs from the first embodiment in that a composite fiber 20A further includes a tubular path 23, and a connecting ferrule 50A includes a conductive path 55A and a fluid path 56. The other components in the second embodiment that are the same as in the first embodiment are given the same reference numerals as those components and will not be described.

The composite fiber 20A includes the tubular path 23, in addition to the first optical fiber 21 and the signal wire 22. The tubular path 23 is a through-portion similar to the signal wire 22. The tubular path 23 is hollow and allows a fluid to flow inside. The connecting ferrule 50A has a plurality of through-holes along the second through-hole 53, which replace the groove(s) 54a in the first embodiment. The through-holes extend from the third end face 51 to the fourth end face 52, similarly to the second through-hole 53. At least one of the through-holes functions as the fluid path 56, and each of the other through-holes is filled with, for example, a conductive material and functions as the conductive path 55A. Similarly to the conductive path(s) 55 in the first embodiment, the conductive path 55A in the present embodiment may be a conductive paste containing a conductive material filling the through-hole, a conductive wire such as a thin metal wire placed and fixed in the through-hole, or a conductive wire buried in a conductive paste in the through-hole.

The stationary ferrule 10 and the connecting ferrule 50A are placed to have the second end face 12 and the third end face 51 abutting each other. In the present embodiment, the second end face 12 and the third end face 51 abut each other and are in contact with each other. The end of the first optical fiber 21 at the second end face 12 is optically coupled to the end of the second optical fiber 60 at the third end face 51. The signal wire 22 in the composite fiber 20 and the conductive path 55A are electrically connected to each other. The tubular path 23 in the composite fiber 20 connects to the fluid path 56. This structure allows liquids such as liquid drugs and fluids such as various gases for experimentation to be fed to brain cells from an external device.

Figure 8A:
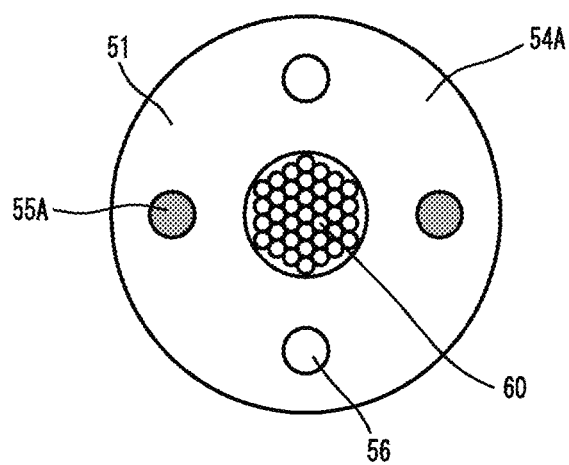
FIG. 8A is an end view of a connecting ferrule according to a third embodiment.
Figure 8B:
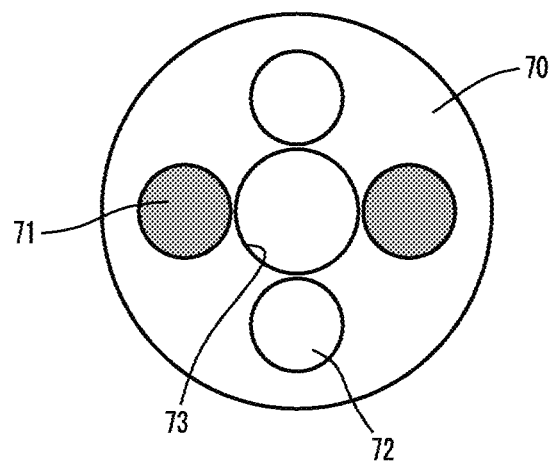
FIG. 8B is an end view of a sealant in the third embodiment.
Figure 9:
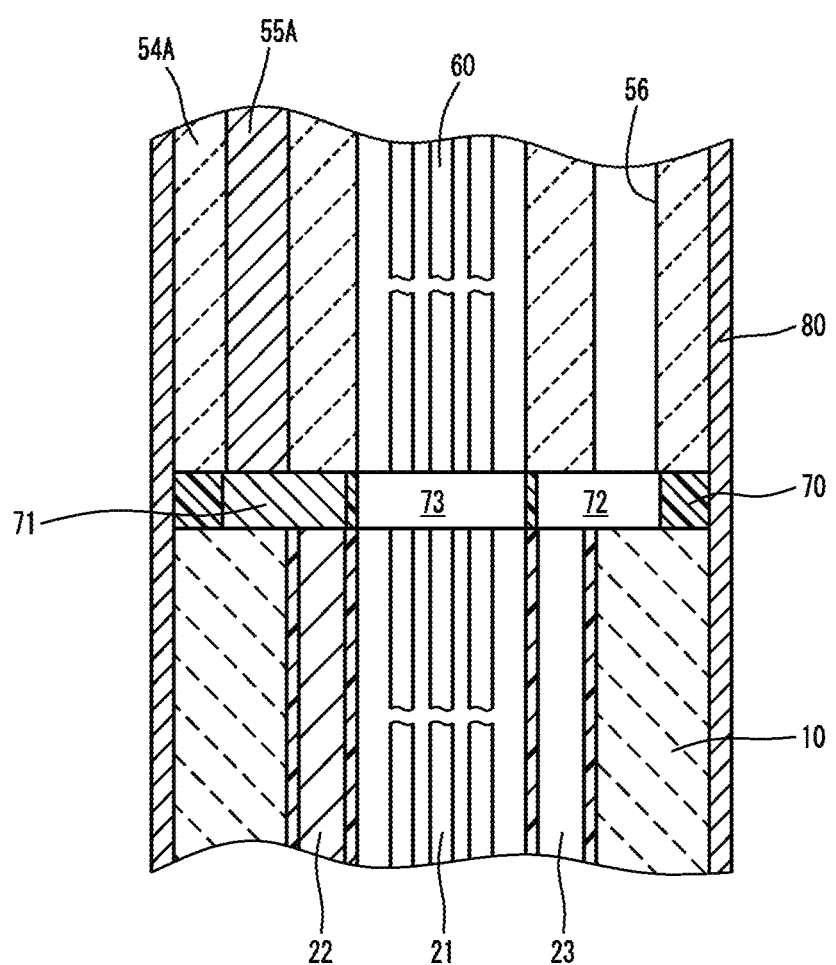
FIG. 9 is a partially enlarged cross-sectional view of a composite fiber connecting assembly according to the third embodiment.

A third embodiment will now be described. FIG. 8A is an end view of a connecting ferrule according to a third embodiment. FIG. 8B is an end view of a sealant in the third embodiment. FIG. 9 is a partially enlarged cross-sectional view of a composite fiber connecting assembly according to the third embodiment. The third embodiment differs from the second embodiment in that a sealant 70 is between the stationary ferrule 10 and the connecting ferrule 50A. The other components in the second embodiment that are the same as in the first embodiment are given the same reference numerals as those components and will not be described. The connecting ferrule 50A may be limited by the size and the position of its conductive path 55A and its fluid path 56 for connection to an external device. The connecting ferrule 50A may thus be unconnectable directly to the signal wire 22 and the tubular path 23 in the composite fiber. Such connection may be achieved using the sealant 70 placed between the second end face 12 of the stationary ferrule 10 and the third end face 51 of the connecting ferrule 50.

The sealant 70 includes a conductive portion 71 for electrically connecting the signal wire 22 to the conductive path 55A, a third through-hole 72 connecting to both the tubular path 23 and the fluid path 56, and a through-hole 73 that serves as a gap enabling optical coupling between the first optical fiber 21 and the second optical fiber 60. The sealant 70 may be formed from any material that resists a fluid such as a liquid drug for experimentation and is both airtight and watertight. The sealant 70 may be, for example, a resin material with relatively low elasticity, such as silicon resin. The conductive portion 71 may be formed from, for example, a conductive resin material. The conductive portion 71 may have an elastic modulus similar to the elastic modulus of the sealant 70 to reduce stress caused by a difference in elastic modulus between the two materials. For highly reliable electrical connection, the conductive portion 71 may have a larger modulus of elasticity than the sealant 70.

A liquid drug to be fed to brain cells through the tubular path 23 and the fluid path 56 may be, for example, a solution containing a virus or a solution containing a toxin. A virus may be injected into the brain for gene expression, or tetrodotoxin (TTX), a toxin found in a pufferfish, may be administered to the brain to stop the nerve function. The activity of brain cells or changes in the brain cells responding to such a liquid drug (drug) or a virus can be observed.

The stationary ferrule 10 and the connecting ferrule 50A are placed to have the second end face 12 and the third end face 51 abutting each other. In the present embodiment, the second end face 12 and the third end face 51 abut each other with the sealant 70 between them. The second end face 12 of the stationary ferrule 10 and the third end face 51 of the connecting ferrule 50 are in contact with the sealant 70. The end of the first optical fiber 21 at the second end face 12 is optically coupled to the end of the second optical fiber 60 at the third end face 51 through the through-hole 73 in the sealant 70. The signal wire 22 in the composite fiber 20 and the conductive path 55A are electrically connected with the conductive portion 71 of the sealant 70. The tubular path 23 in the composite fiber 20 and the fluid path 56 connect to each other through the through-hole 72 in the sealant 70.

The external device may be, for example, an electroencephalogram (EEG) device to obtain information about the activity of brain tissue as an electrical signal using the composite fiber connecting assembly 100. The external device may be a device that transmits and receives optical signals, such as an image recognition device, an imaging device, or a light emitting device. Such devices provide images to allow visual observation of changes in the brain cells. The imaging process may be further facilitated by light illumination. The brain cells may be optically stimulated to have their responses obtained as electrical signals or images.

The devices may be specifically as follows. An EEG device may be used to measure electrical signals. An isolator may be used to transfer electricity. The device can measure electrical signals representing the activity of nerve cells. A photodetector or a photomultiplier tube may be used to measure light. To view or record light as an image, a camera may be used to capture or view an image through an objective lens. A laser diode or a laser-emitting diode (LED) may be used to provide optical stimulation. For example, visible light may be used for stimulation. A fluid to be fed may be a liquid drug to be fed using a syringe pump. A tube 94 may be a resin tube of, for example, polyethylene. The tube can be used for dispensing or sucking a fluid.

Figure 10:
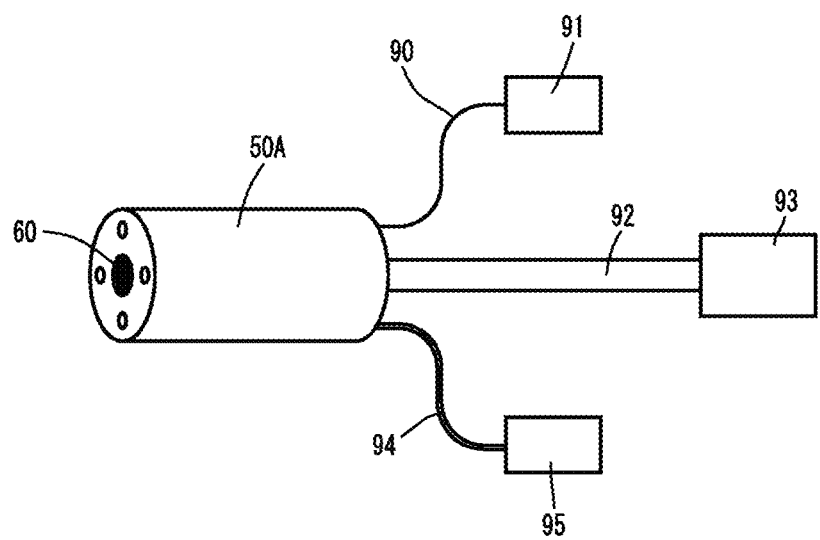
FIG. 10 is a schematic view of a composite interface device for experimentation on living animals.

FIG. 10 is a schematic view of a composite interface device for experimentation on living animals. The composite interface device for experimentation on living animals includes, in addition to the connecting ferrule 50 and the second optical fiber 60, a lead wire 90 electrically connected to the conductive path 55A, a connector terminal 91 for connecting the lead wire 90 to an external device, a third optical fiber 92 optically connected to the second optical fiber 60, a connector terminal 93 for connecting the third optical fiber 92 to the external device, the tube 94 connected to the fluid path 56, and a connector terminal 95 for connecting the tube 94 to the external device. The connecting ferrule 50 and the second optical fiber 60 are connected to the stationary ferrule 10 and the composite fiber 20 fixed beforehand to the brain of a living animal for experimentation to allow connection between the brain of the living animal for experimentation and the external device.

Although the measurement sites are the scalp 30, the skull 31, a dura mater 32, and the brain 34 in the above embodiments, the measurement sites may be other parts of a living body that can be fixed with a bond similar to the bond 37 described above. The composite fiber connecting assembly according to the above embodiment may be used to observe, for example, blood vessels or digestive organs, without being fixed in a manner immovable in the living body. Further, the stationary ferrule and the ferrule body of the connecting ferrule may have circular or polygonal cross-sections perpendicular to the central axis, such as square, triangular, or pentagonal cross-sections. The cross-sections of the stationary ferrule and the ferrule body may be basically circular with the circumference either partially or asymmetrically straight, or specifically may be, for example, D-shaped or substantially elliptical cross-sections perpendicular to the axis, and may include a flat circumference portion or a flat axisymmetric portion. The stationary ferrule and the ferrule body with such flat portions can be held easily with, for example, tweezers, and thus can be handled easily.

The present disclosure may be embodied in various forms without departing from the spirit or the main features of the present disclosure. The embodiments described above are thus merely illustrative in all aspects. The scope of the present invention is defined not by the description given above but by the claims. Any modifications and alterations contained in the claims fall within the scope of the present invention.

REFERENCE SIGNS LIST 10 stationary ferrule
11 first end face
12 second end face
13 first through-hole
20 composite fiber
20A composite fiber
21 first optical fiber
22 signal wire
23 tubular path
24 first end portion
25 second end portion
30 scalp
31 skull
32 dura mater 34 brain
37 bond
50 connecting ferrule
50A connecting ferrule
51 third end face
52 fourth end face
53 second through-hole
54 ferrule body
54a groove
55 conductive path
55A conductive path
56 fluid path
60 second optical fiber
70 sealant
71 conductive portion
72 through-hole
73 through-hole
80 sleeve
90 lead wire
91 connector terminal
92 third optical fiber
93 connector terminal
94 tube
95 connector terminal
100 composite fiber connecting assembly

The invention claimed is:

1. An optical connector ferrule, comprising:
a first ferrule being tubular and having a first end face, a second end face opposite to the first end face, and a first through-hole extending from the first end face to the second end face;
a composite fiber including a first optical fiber and a plurality of electrically conductive signal wires along the first optical fiber, the composite fiber having a first end portion extending to the second end face and placed in the first through-hole; and
a second ferrule including a ferrule body being tubular and a linear portion, the ferrule body having a third end face, a fourth end face opposite to the third end face, and a second through-hole extending from the third end face to the fourth end face, the linear portion extending from the third end face along the second through-hole,
wherein the second end face and the third end face abut each other,
the plurality of electrically conductive signal wires and the linear portion are connected to each other wherein the plurality of electrically conductive signal wires are inside resin which surrounds the optical fiber, such that the plurality of electrically conductive signal wires and the optical fiber are separated, and
wherein an exterior of the second ferrule includes a plurality of grooves which extend axially around the second through-hole and the linear portion is inside each of the plurality of grooves.

2. The optical connector ferrule according to claim 1, wherein
the linear portion includes a conductive path electrically connectable to the plurality of electrically conductive signal wires.

3. The optical connector ferrule according to claim 1, wherein
the plurality of electrically conductive signal wires includes a tubular path, and
the linear portion includes a path connecting to the tubular path.

4. The optical connector ferrule according to claim 3, further comprising:
a sealant between the second end face and the third end face,
wherein the sealant has a third through-hole connecting to the tubular path and to the path.

5. The optical connector ferrule according to claim 1, wherein
at least one of the first ferrule or the ferrule body comprises zirconia.

6. An optical connector, comprising:
the optical connector ferrule according to claim 1; and
a sleeve enclosing an area in which the second end face and the third end face abut each other.

7. A composite fiber connecting assembly, comprising:
the optical connector according to claim 6; and
a second optical fiber in the second through-hole to optically couple a first end of the first optical fiber and a third end of the second optical fiber at the third end face of the ferrule body.

8. The optical connector ferrule according to claim 1, wherein
the composite fiber protrudes axially outward from the first end face.

* * * * *